US007996241B2

(12) United States Patent
Zak et al.

(10) Patent No.: US 7,996,241 B2
(45) Date of Patent: Aug. 9, 2011

(54) PROCESS, KNOWLEDGE, AND INTELLIGENCE MANAGEMENT THROUGH INTEGRATED MEDICAL MANAGEMENT SYSTEM FOR BETTER HEALTH OUTCOMES, UTILIZATION COST REDUCTION AND PROVIDER REWARD PROGRAMS

(76) Inventors: Solomon Zak, St Louis Park, MN (US); Rudra Duddala, Westboro, MA (US); Craig Johnson, Cambrige, MN (US); Poladas James, Worcester, MA (US); Madusudhana Narahari, Whitinsville, MA (US); Bala Ankarfa, Westboro, MA (US); Streesha Parvatham, Westboro, MA (US); Sashidhar Kokku, Westboro, MA (US)

( * ) Notice: Subject to any disclaimer, the term of this patent is extended or adjusted under 35 U.S.C. 154(b) by 476 days.

(21) Appl. No.: 12/118,768

(22) Filed: May 12, 2008

(65) Prior Publication Data
US 2009/0281826 A1 Nov. 12, 2009

(51) Int. Cl.
*G06Q 10/00* (2006.01)
*G06Q 50/00* (2006.01)
(52) U.S. Cl. .................................. 705/2; 705/3; 705/4
(58) Field of Classification Search .................. 705/2–4
See application file for complete search history.

(56) References Cited

U.S. PATENT DOCUMENTS

| | | | |
|---|---|---|---|
| 5,301,105 A | 4/1994 | Cummings, Jr. | |
| 5,845,254 A | 12/1998 | Lockwood et al. | |
| 2002/0111826 A1* | 8/2002 | Potter et al. ........................ | 705/2 |
| 2003/0135394 A1 | 7/2003 | Padron et al. | |
| 2004/0107134 A1 | 6/2004 | Nelson et al. | |
| 2006/0149596 A1 | 7/2006 | Surpin et al. | |
| 2007/0078680 A1* | 4/2007 | Wennberg ........................ | 705/2 |

OTHER PUBLICATIONS

Lowes, How Your Productivity is Measured: If You're Paid Based on Your Output, You Should Find Out What Goes Into the Calculation and Whether the Formula Is Best for You, Oct. 2007, Medical Economics, pp. 24-30.*

* cited by examiner

*Primary Examiner* — Luke Gilligan
(74) *Attorney, Agent, or Firm* — Ash Tankha; Lipton, Weinberger & Husick

(57) ABSTRACT

Disclosed herein is a computer implemented method and system for rewarding health care providers using an integrated medical management system. A web application analyzes performance of the health care providers. The web application acquires information from integrated medical management system. The acquired information includes information of health care quality improvement analysis, disease and case based management, utilization analytics, physician profiling, authorizations management, lab and imaging information, and health risk assessment information. The web application determines performance indices for the health care providers based on the acquired information. The performance indices include a quality index, an economic index, and a relative value unit index of the health care providers. The web application analyzes the performance of the health care providers based on the performance indices. The analysis includes identifying health care providers eligible for a reward. The health care providers are then rewarded based on the analyzed performance.

24 Claims, 8 Drawing Sheets

PROCESS, KNOWLEDGE, AND INTELLIGENCE MANAGEMENT THROUGH INTEGRATED MEDICAL MANAGEMENT SYSTEM FOR BETTER HEALTH OUTCOMES, UTILIZATION COST REDUCTION AND PROVIDER REWARD PROGRAMS

CROSS REFERENCE TO RELATED APPLICATIONS

The following patents are incorporated herein as references:
1. Non provisional patent application with patent number U.S. Ser. No. 11/895,319 titled "Prospective Health Care Quality Improvement", filed on Aug. 25, 2007 at the United States Patent and Trademark Office.
2. Non provisional patent application with patent number U.S. Ser. No. 11/973,754 titled "Method And System Of Utilization Analysis And Physician Profiling In A Health Care Organization", filed on Oct. 10, 2007 at the United States Patent and Trademark Office.
3. Non provisional patent application with patent number U.S. Ser. No. 12/001,176 titled "Online Disease And Case Management System", filed on Dec. 10, 2007 at the United States Patent and Trademark Office.

BACKGROUND

This invention, in general, relates to a health care organization. More particularly, this invention relates to rewarding health care providers in a health care organization based on performance of the health care providers.

Health care organizations, typically, include health care providers and members enrolled for a health plan in the health care organization. The operations of a health care organization depend on one or more factors including the number of members enrolled for the health plans, performance of the health care providers, quality of service provided by the health care providers to the enrolled members, management and utilization of the resources of the health care organization, etc. For maintaining quality of service in the health care organization, the performance of the health care providers needs to be monitored periodically. Furthermore, for improving quality in the health care organization, the health care providers need to be engaged and motivated for improving their performance.

Therefore, there is a need for rewarding health care providers in a health care organization based on performance of the health care providers.

SUMMARY OF THE INVENTION

This summary is provided to introduce a selection of concepts in a simplified form that are further described in the detailed description of the invention. This summary is not intended to identify key or essential inventive concepts of the claimed subject matter, nor is it intended for determining the scope of the claimed subject matter.

The computer implemented method and system disclosed herein addresses the above stated need for rewarding health care providers in a health care organization based on performance of the health care providers.

The computer implemented method and system disclosed herein provides a web application for analyzing performance of the health care providers. The health care providers include primary care physicians, procedurally related group specialists, medically related groups specialists, provider networks, hospitals, and ancillary providers. The web application acquires information from multiple medical management systems. The medical management systems include a utilization analytics system, provider profiling system, an intelligent health care quality improvement system, a disease and case based management system, referrals and authorizations management system, and a health risk assessment system.

The acquired information includes intelligent health care quality improvement analysis information, disease and case based management information, utilization analytics information, physician profiling information, authorizations management information, lab and imaging information, and health risk assessment information. The acquired information further includes information of members enrolled with the health care providers. The information of the members includes information of health plan benefits, medical claims, pharmacy claims, hospital information, allied health centers information, authorizations and referrals information, lab and imaging information, disease conditions, and comorbid conditions of the members.

Further, the web application determines performance indices for the health care providers based on the acquired information. The web application analyzes the performance of the health care providers based on the determined performance indices. The performance analysis also includes identifying health care providers eligible for a reward. Further, the method and system disclosed herein rewards the identified health care providers based on the analyzed performance.

The web application enables the health care providers to update unobserved performed health care measures. The web application monitors the performance of the health care providers and further identifies ineffective health care providers. The ineffective health care providers are provided recommendations for improvement on health care management in order to improve the performance. By monitoring and analyzing the performance of the health care providers, the health care organization reduces medical costs and increases quality of care to the enrolled members.

BRIEF DESCRIPTION OF THE DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and instrumentalities disclosed herein.

DETAILED DESCRIPTION OF THE INVENTION

Figure 1:
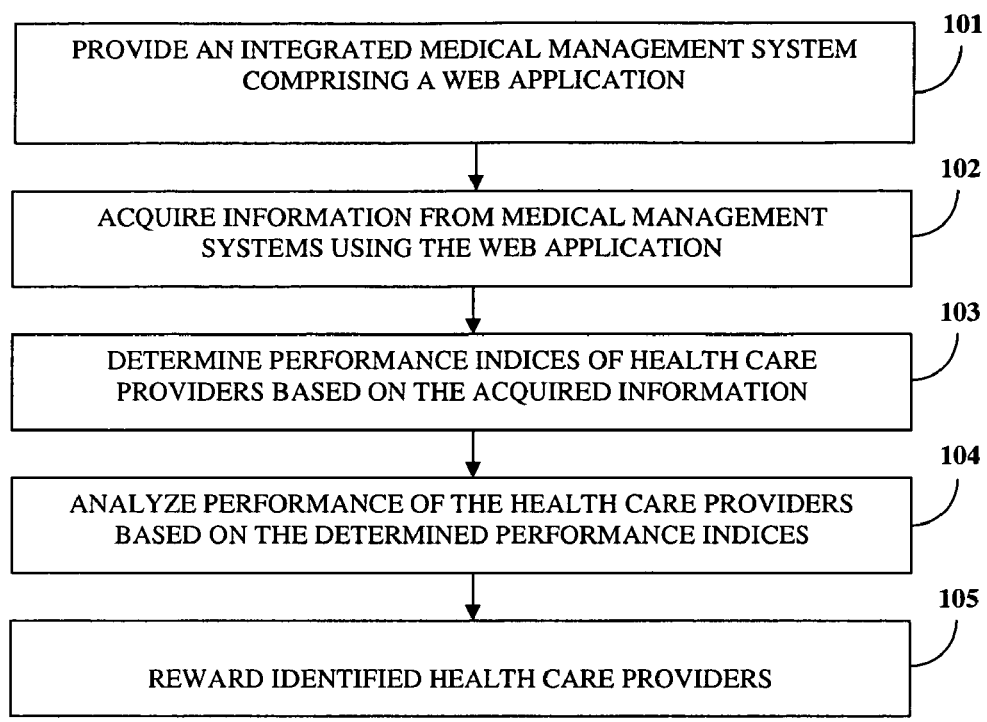
FIG. 1 illustrates a computer implemented method of rewarding health care providers in a health care organization using an integrated medical management system.

FIG. 1 illustrates a computer implemented method of rewarding health care providers 201 in a health care organization using an integrated medical management system 213. The method disclosed herein provides 101 an integrated medical management system 213. The integrated medical management system 213 comprises a web application for analyzing performance of the health care providers 201. The web application is exemplarily illustrated in FIG. 4. The health care providers 201 include primary care physicians (PCPs) 601, procedurally related group specialists, medically related groups specialists, provider networks, hospitals, and ancillary providers. The web application acquires 102 information from multiple medical management systems 204.

The medical management systems 204 include a utilization analytics system 204a, an intelligent health care quality improvement (IHCQI) system 204b, a disease and case based management system 204c, provider profiling system 204d, referrals and authorizations management system 204e, and a health risk assessment system 204f. The acquired information includes IHCQI analysis information, disease and case based management information, utilization analytics information, physician profiling information, authorizations management information, lab and imaging information, and health risk assessment information. The acquired information further includes information of members 302 enrolled with the health care providers 201. The information of the members 302 includes information of health plan benefits, medical claims, pharmacy claims, hospital information, allied health centers information, authorizations and referrals information, lab and imaging information, disease conditions, and comorbid conditions of the members 302.

The utilization analytics system 204a analyzes health care data for utilization analysis of the health care providers 201. The health care data includes health plan information of members 302 of the health care organization, information of the health care providers 201, claims information, and the hospital information. The health care data is translated and organized in a structured relational format in a set of standard tables. The standard tables include a member data table, a provider data table, a claims data table, a hospital data table, a global table, a parameter table, and a proprietary table.

The global table includes information on standard codes such as current procedure terminology (CPT) code, international classification of diseases (ICD9) diagnosis code, a health care common procedure coding system (HCPCS) code, a revenue code, an ICD9 procedure code, a national drug classification (NDC) code, and a diagnosis related groups (DRG) code. The organized health care data is analyzed by calculating member statistics for a health plan using the health plan information of the members 302. The claims of the members 302 are processed to classify the claims based on age, gender, disease, and comorbid conditions of the members 302. Costs incurred by the health care organization are determined using one or more of the health plan information of the members 302, the information of the health care providers 201, the claims information, and the hospital information.

The IHCQI system 204b defines predetermined measures of health care provided by the health care organization. The predetermined measures of health care are defined by the health plan employer data and information set (HEDIS). The predetermined measures are divided into eight domains namely, effectiveness of care, availability of care, satisfaction with the experience of care, health plan stability, use of services, cost of care, informed health care choices, and health care descriptive information. The predetermined measures specify how health care organizations collect, audit and report performance information across clinical areas.

The IHCQI system 204b may comprise immunizations, cancer screenings, treatment after heart attacks, diabetes, asthma, flu shots, access to services, dental care, alcohol and drug dependence treatment, timeliness of handling claims and phone calls, prenatal and postpartum care, mental health care, preventive visits, inpatient utilization, drug utilization, and distribution of the members 302 by age, gender, product lines etc. The IHCQI system 204b may be implemented in the health care organization for periodic reporting such as weekly or monthly reporting. For example, the IHCQI system 204b may be implemented at the beginning of the current year in the health care organization to proactively identify the members 302 due for health care. The IHCQI system 204b prospectively determines plan level, provider level, and member level performance of HEDIS measures in the current year, whereas standard HEDIS implementation retrospectively determines plan level performance of HEDIS measures in the previous year.

The disease and case based management system 204c is used for disease based management of medical care to the patients. The information of the patients is retrieved from multiple information sources using the disease and case based management system 204c. The multiple information sources may be one or more of claims data, health risk questionnaires, and utilization analytics data. The retrieved information of the patients is used to identify a disease condition of the patient population. The disease condition of the patient population is identified by utilizing at least one of diagnostic codes and service codes including ICD9 codes in a medical or pharmacy claim, lab and imaging values in the lab and imaging report, clinical values in an authorization request, information provided by the patients in a health risk questionnaire, and information provided by the patients in a patient survey.

The disease and case based management system 204c is also used for case based management of medical care to a member. The member may be a patient enrolled for a health plan with the health care organization. The information of the member is retrieved from multiple information sources using the disease and case based management system 204c. The retrieved information of the member is used to identify a member with a disease condition. The identified member enrolls for the case based management of medical care. The enrolled member is managed by a case manager. The case manager provides personalized support to the enrolled member. The enrolled member is educated about the disease condition for self monitoring of the disease condition. The status of the self monitored disease condition is recorded in a disease log of personal health records on the disease and case based management system 204c by the member. Based on the recorded status, visits are scheduled to the health care provider for medical treatment of the enrolled member. Further, the enrolled member is monitored for medical progress based on the medical treatment.

The provider profiling system 204d enables the health care organization to compare PCPs 601 practice patterns across various health care dimensions. The health care dimensions such as cost, service and resource utilization data are used for measuring quality of the PCPs 601. The referrals and authorizations management system 204e is used for managing referrals and authorizations. A referral is the process of sending a patient to another health care provider for health care service that the referring person believes is necessary. An authorization is a process of reviewing the medical necessity for certain health services prior to the health care services being rendered. The health risk assessment system 204f is used for early detection and prevention of medical conditions and diseases.

The web application determines 103 performance indices for the health care providers 201 based on the acquired information. The performance indices include a quality index, an economic index, and a relative value unit (RVU) index. The quality index is determined based on HEDIS analysis, disease management, and other quality of health care measures. The economic index is determined based on utilization analytics, physician profiling, and authorizations management. The RVU index is determined based on actual utilization of relative value units.

Figure 4:
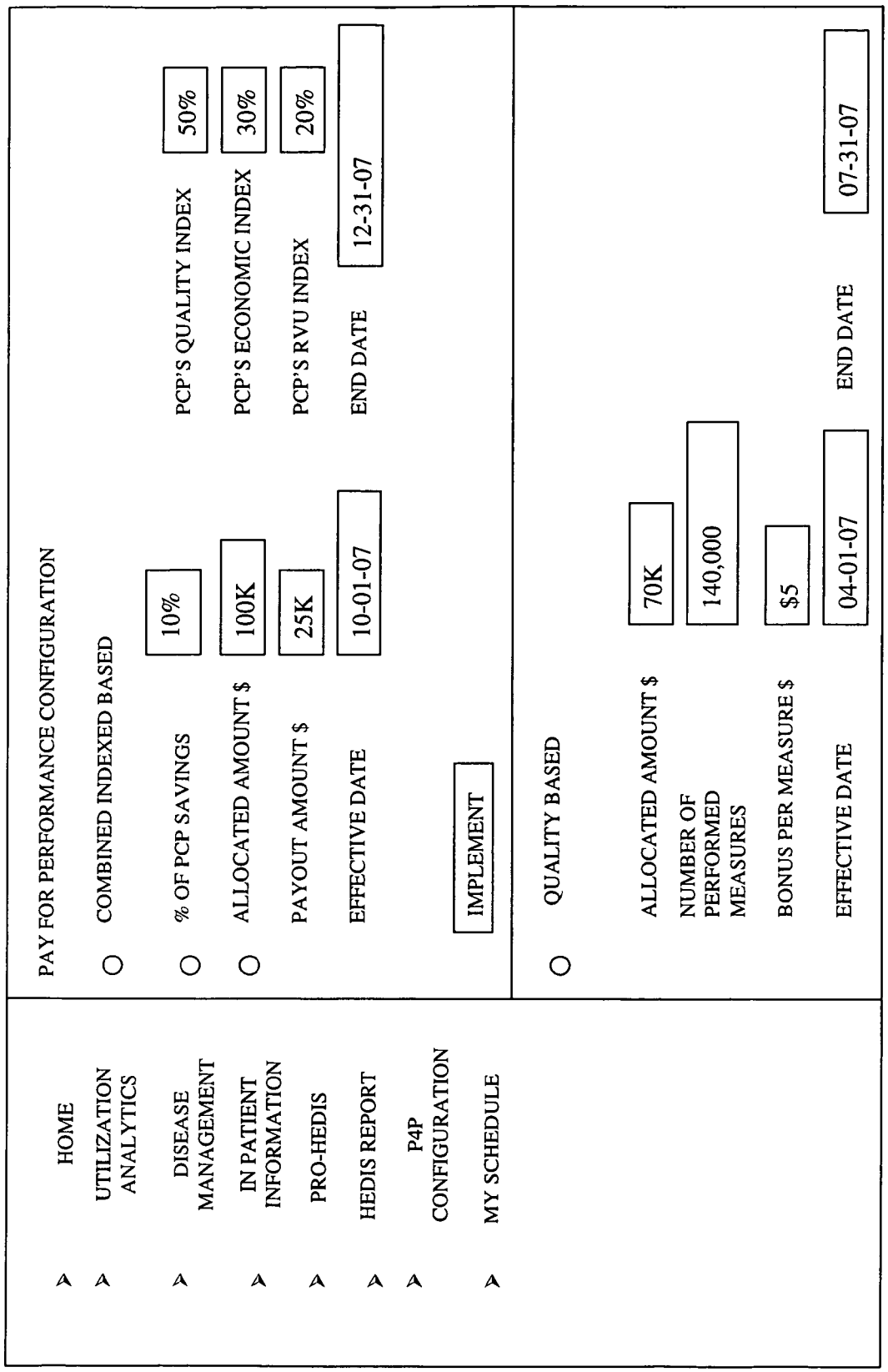
FIG. 4 exemplarily illustrates a pay for performance web application.

Health care administrators such as medical directors configure pay for performance using the web application in order to assign a predetermined weighted percentage value for each of the performance indices. Exemplarily, a percentage weighted value of 50% as the quality index, a percentage weighted value of 30% as the economic index, and a percentage weighted value of 20% as the RVU index may be assigned as illustrated in FIG. 4. The health care administrators may assign a bonus amount for each performed measure by the physician. Further, an allocated amount may be calculated by multiplying the bonus amount with the number of performed measures. Exemplarily, a bonus amount of 5 dollars multiplied by 140000 performed measures will provide an allocated amount of 700000 dollars as illustrated in FIG. 4. The performance indices may be calculated for a predetermined period of time. The predetermined period may be calculated from an "effective date" until an "end date" as exemplarily illustrated in FIG. 4.

Further, the web application analyzes 104 the performance of the health care providers 201 based on the determined performance indices. The analysis includes identifying the health care providers 201 eligible for a reward. The method disclosed herein rewards 105 the identified health care providers 201 based on the analyzed performance. Reports on the performance of the health care providers 201 are generated using the web application. The health care providers 201 are offered a projected increase in reimbursements for ensuring reduced medical costs and increased quality of care to the members.

The web application enables the health care providers 201 to update unobserved performed health care measures. The health care providers 201 identify the members 302 who have not undergone the updated health care measures using the web application. The web application identifies health care due members 302 and notifies the health care due members 302 automatically and periodically to undergo medical treatment. The health care due members 302 are notified via electronic mail (email), voice recorded messages, or phone. The web application notifies the health care providers 201 for performing the health care measures. Further, the health care providers 201 are notified via email or fax for performing the health care measures on the members 302. The web application automatically schedules appointments with the health care providers 201 upon detection of abnormal condition of a member enrolled for the health plan.

The integrated medical management system 213 automatically triggers different communication devices for notifying the health care providers 201 in absence of access to the web application. For example, if the health care providers 201 do not log onto the web application, the integrated medical management system 213 intelligently triggers a fax machine to generate faxes at the health care provider's 201 office. Furthermore, if the members 302 do not log onto the web application, the integrated medical management system 213 intelligently sends a phone message to the members 302. The phone message comprises a generic message without the member's health information, if an answering machine answers a phone call. On authentication of the member using an identifier number, the actual message is delivered. Therefore, all communications using the integrated medical management system 213 are health insurance portability and accountability act (HIPAA) compliant. Moreover, personal health information is not communicated unless the member provides a secured log in information for electronic mails or authenticates using an identifier for phone communications.

The integrated medical management system 213 also receives medical information of members 302 via different communication devices in absence of access of the web application by the health care providers. The integrated medical management system 213 then associates the received information received with the health care providers 201. The integrated medical management system 213 then enables updation of the received information. For example, consider a health care provider, wishes to update information about a member's medical information. The information to be updated may be in the patient's chart. The health care provider may send a copy of the patient chart via a fax machine, in case, the health care provider does not have access to the web application. The integrated medical management system 213 intelligently associates the faxed information with the health care provider's file since the fax number of the health care provider is stored in the health care provider's file in the integrated medical management system 213. A health plan staff may then update the information of the member and may also attach the faxed information for proof.

The web application displays multiple lists including a list of eligible members 302 and associated PCPs 601 of the eligible members 302 based on the member's demographics and disease conditions, a list of eligible members 302 who need to be tested based on a particular health care measure or a particular disease, a list of PCPs 601 who have updated the performance measures, and a list of PCPs 601 who have not logged into the web application. The web application enables the health care organization to compare analyzed performance of the health care providers 201 with performance standards defined by performance evaluation organizations such as the national committee for quality assurance (NCQA).

The web application monitors the performance of the health care providers 201 and further identifies ineffective health care providers 201. The identified ineffective health care providers 201 are provided recommendations for improvement on health care management. By monitoring and analyzing the performance of the health care providers 201, the health care organization reduces medical costs and increases quality of care to the enrolled members 302.

Figure 2:
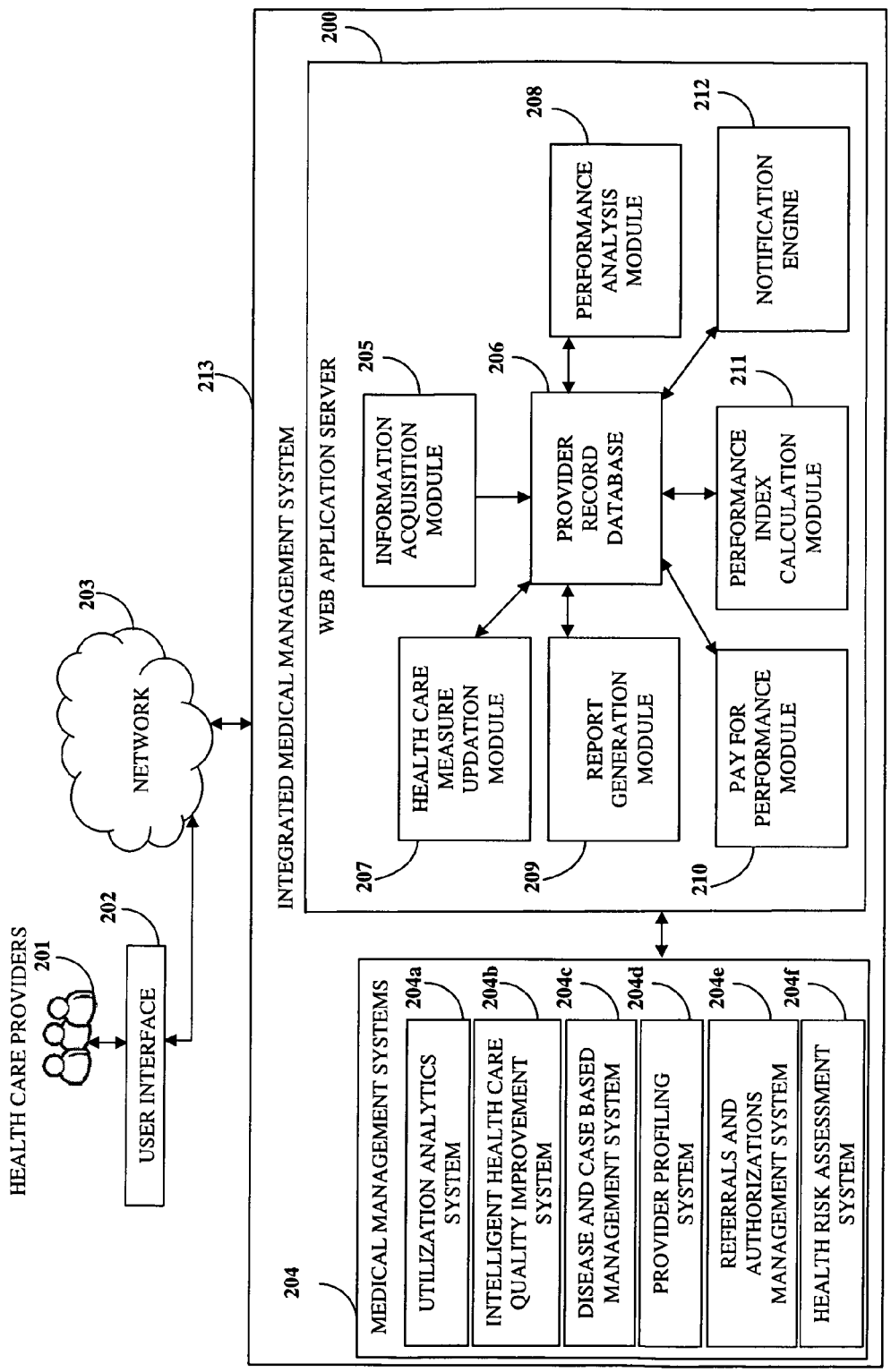
FIG. 2 illustrates a computer implemented system for rewarding health care providers in a health care organization using an integrated medical management system.

FIG. 2 illustrates a computer implemented system for rewarding health care providers 201 in a health care organization using an integrated medical management system 213. The system disclosed herein comprises a user interface 202 and an integrated medical management system 213, connected via a network 203. The integrated medical management system 213 enables updation of medical information of members received via different communication devices. The integrated medical management system 213 comprises multiple medical management systems 204 and a web application server 200. The web application server 200 hosts a web application for analyzing the performance of the health care providers 201. The health care providers 201 access the web application via the user interface 202. The web application server 200 comprises an information acquisition module 205, a provider record database 206, a health care measure updation module 207, a performance analysis module 208, a report generation module 209, a pay for performance module 210, a performance index calculation module 211, and a notification engine 212.

The information acquisition module 205 acquires information from the medical management systems 204. The medical management systems 204 include a utilization analytics system 204a, an intelligent health care quality improvement (IHCQI) system 204b, a disease and case based management system 204c, provider profiling system 204d, referrals and authorizations management system 204e, and a health risk assessment system 204f. The acquired information includes IHCQI analysis information, disease and case based management information, utilization analytics information, physician profiling information, authorizations management information, lab and imaging information, and health risk assessment information. The medical management systems 204 are further explained in the detailed description of FIGS. 5-7.

The acquired information further includes information of members 302 enrolled with the health care providers 201. The information of the members 302 includes information of health plan benefits, medical claims, pharmacy claims, hospital information, allied health centers information, authorizations and referrals information, lab and imaging information, disease conditions, and comorbid conditions of the members 302. The health care measure updation module 207 updates unobserved performed health care measures of the members 302 enrolled for the health plan. The web application enables the health care providers 201 to update the unobserved performed health care measures via the user interface 202.

The performance index calculation module 211 determines performance indices for the health care providers 201. The performance indices include a quality index, an economic index, and an RVU index of the health care providers 201. The user interface 202 enables the health care administrators such as medical director to assign a predetermined weighted percentage value for each index. For example, a PCP may be assigned a percentage value of 50% for the quality index, a percentage value of 30% for the economic index, and a percentage value of 20% for the RVU index.

The performance analysis module 208 analyzes and monitors the performance of the health care providers 201. The report generation module 209 generates reports on the performance of the health care providers 201. The pay for performance 210 rewards the health care providers 201 based on the analyzed performance. The provider record database 206 stores the acquired information, updated health care measure information, generated reports, information of the determined performance indices, analyzed performance information of the health care providers 201, and reward information of the health care providers 201. The notification engine 212 notifies the health care providers 201 to perform the health care measures.

Figure 3:
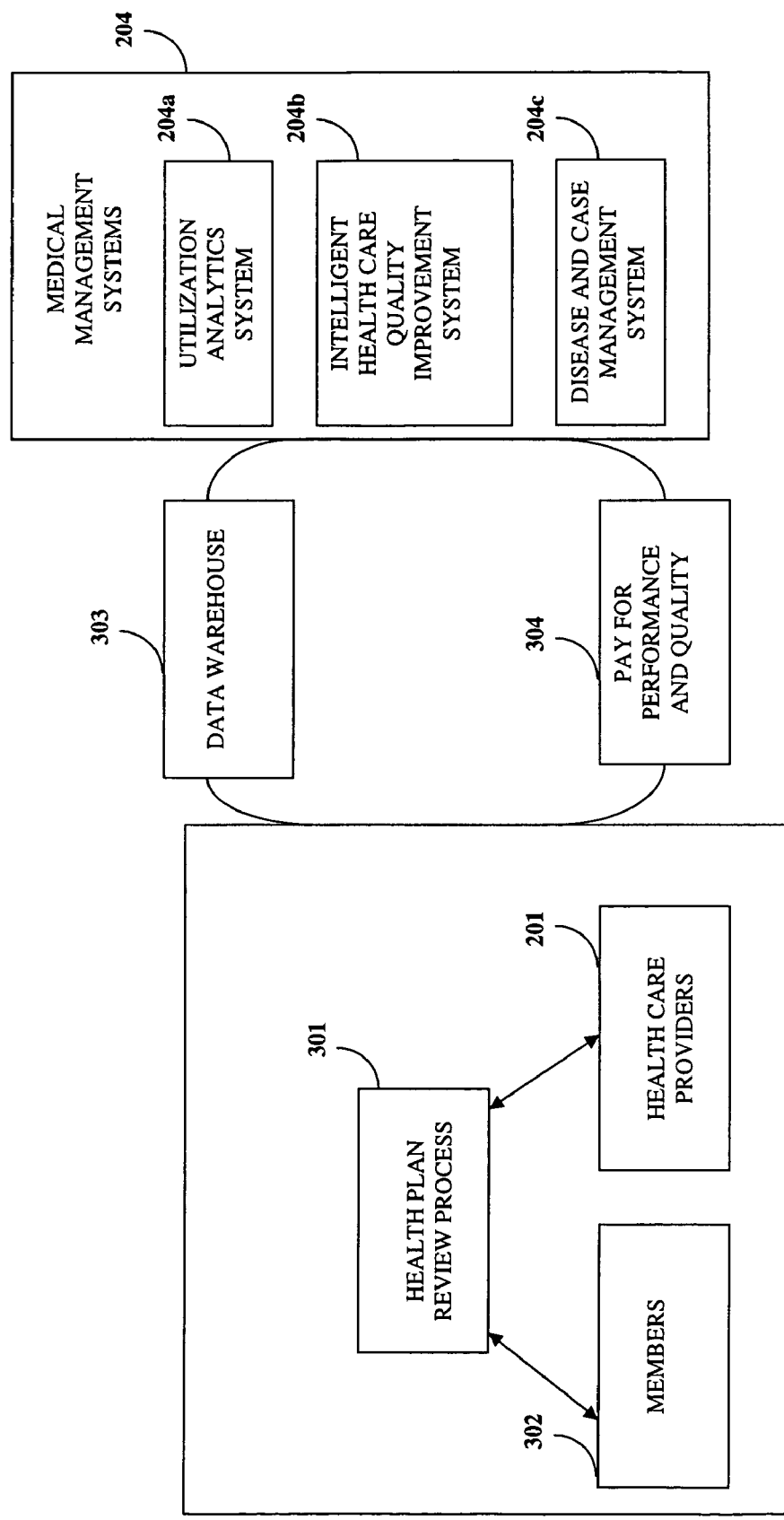
FIG. 3 exemplarily illustrates the work flow process involved in monitoring and analyzing the performance of the health care providers.

FIG. 3 exemplarily illustrates the work flow process involved in monitoring and analyzing the performance of the health care providers 201. A data warehouse 303 stores information acquired from the medical management systems 204 and multiple databases. The medical management systems 204 include the utilization analytics system 204a, the IHCQI system 204b, and the disease management and case management system 204c.

Upon acquiring the information from the medical management systems 204, a health plan review process 301 of the health care providers 201 is performed. The health plan review process 301 includes periodic performance review of the health care providers 201, creating incentive programs for the health care providers 201 and the members 302, and rewarding effective health care providers 201. Further, the health plan review process 301 includes motivating ineffective health care providers 201 to login to the web application and understand current performance scores and methods to improve quality and reduce costs, and educating the members 302. Furthermore, the health plan review process 301 includes coordinating between the members 302 and the health care providers 201 to comply with the IHCQI system 204b measures and disease management protocols.

Further, the health care providers 201 periodically review quality and economic performance, update the IHCQI system 204b and disease and case based management system 204c measures, motivate members 302, and review improvement in performance. The work flow includes paying 304 the health care providers 201 for performance and quality of service.

Figure 5:
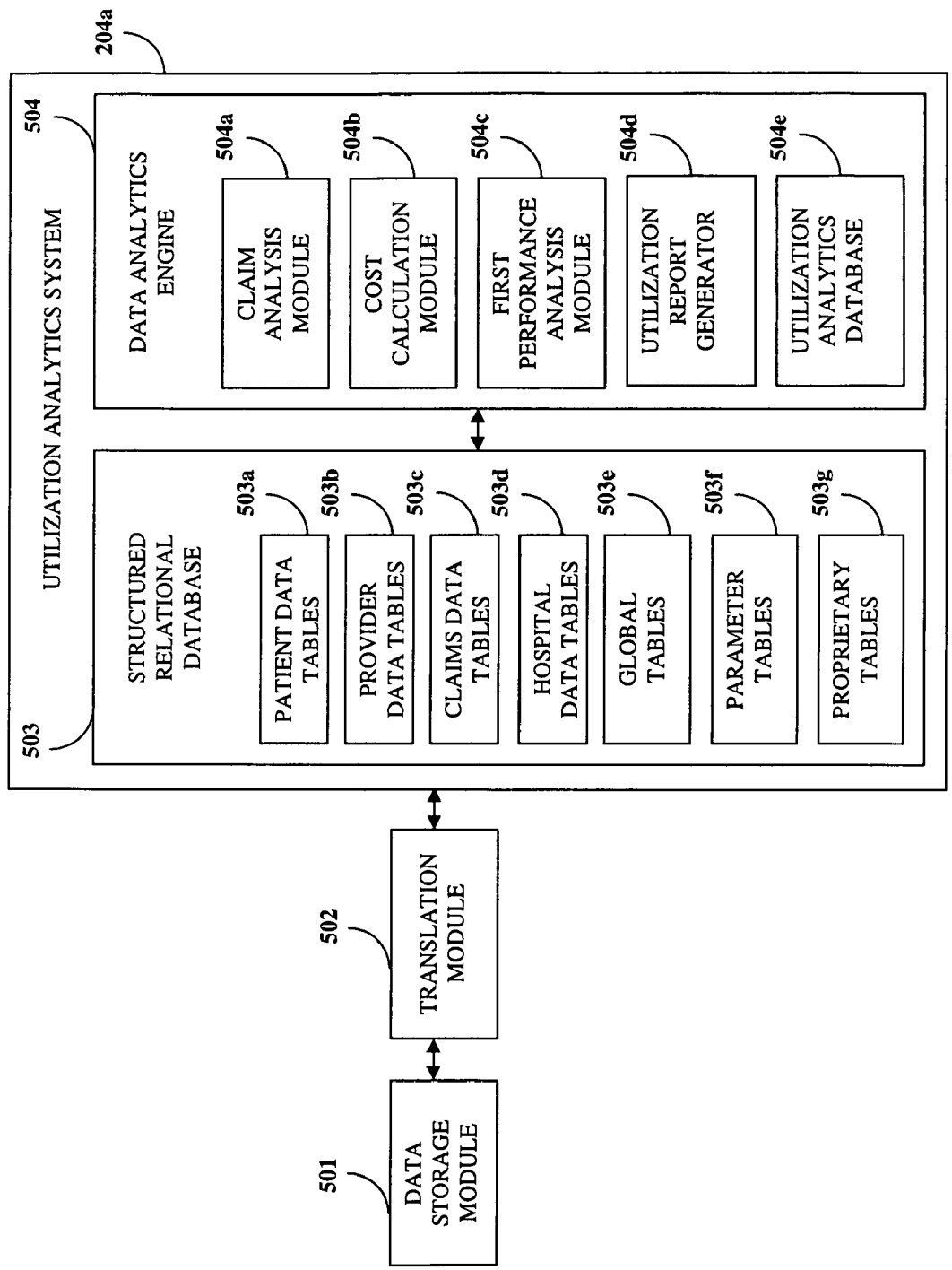
FIG. 5 illustrates a utilization analytics system in a health care organization.

FIG. 5 illustrates a utilization analytics system 204a in a health care organization. The utilization analytics system 204a comprises a structured relational database 503 and a data analytics engine 504. A translational module 501 translates and organizes raw health care data in a structured relational format. The raw health care data includes health plan information of the members 302 of the health care organization, information of the health care providers 201, claims information, and the hospital information. The health care providers 201 include PCPs 601, procedurally related group specialists, medically related groups specialists, provider networks, hospitals, and ancillary providers. The utilization analytics system 204a performs utilization analysis of the PCPs 601.

A data storage module 501 stores the raw health care data. The translation module 502 creates file layouts, mapping fields of the health care data, and verifies for integrity and validity of the health care data. The translated health care data is stored in a structured relational format in the structured relational database 503. The structured relational database 503 comprises member data tables 503a, provider data tables 503b, claims data tables 503c, hospital data tables 503d, global tables 503e, parameter tables 503f, and proprietary tables 503g. The data analytics engine 504 comprises a claim analysis module 504a, a cost calculation module 504b, a first performance analysis module 504c, a utilization report generator 504d, and a utilization analytics database 504e.

The claim analysis module 504a processes the claims of the members 302 enrolled for a health plan. The claims are processed to classify the claims based on age, gender, disease, and comorbid conditions of the member. The claim analysis module 504a further generates a claim summary of the processed claims. The cost calculation module 504b determines costs involved in providing health care services to the members 302 in a health plan. The costs are determined using at least one or more of the health plan information of the members 302, the health care providers 201, the claims, and the hospitals. The costs comprise billed amounts, utilization costs, liability costs, and paid costs. The cost calculation module 503b assigns a catastrophic value to the claims based on the determined costs.

The first performance analysis module 504c assesses the performance of a health care provider using the determined costs. The first performance analysis module 504c is used to analyze the PCPs 601 based on the number of members 302 associated with the PCPs 601. The total cost of all the members 302 in a PCP's practice is determined by the cost calculation module 503b and reported as the PCP's expense. The PCPs' comparative expense indicates the efficiency of the PCP in managing the members' hospitalization and specialist service needs. The first performance analysis module 504c evaluates the performance of the PRG specialists and the MRG specialists by analyzing the costs involved in performing medical procedures and managing medically by the specialist on the members 302. Further the first performance analysis module 504c may assign a performance index to each of the health care providers 201 using the comparative cost analysis data of the health care providers 201.

The first performance analysis module 504c further calculates a utilization performance ratio of the PCP. An average cost is determined for the particular disease condition for a particular age and gender of the members 302. Further, an expected cost for a PCP is determined based on age, gender, and disease conditions of all the PCP's members by a case mix adjustment. The actual cost of all the PCP's members is determined and the ratio of actual cost over the expected cost is reported as the PCP index. The first performance analysis module 504c calculates a composite index value for the PCP. The composite index value is determined by including a predetermined portion of the catastrophic value to the utilization performance ratio of the PCP. The first performance analysis module 504c further calculates an RVU utilization for the PCP by using service codes with the RVU and applying proprietary methodology for service codes that do not have the RVU.

The utilization report generator 504d generates web reports of the utilization analysis of the PCPs 601. The generated reports include admin actuarial reports, PCP analysis reports, PRG specialists analysis reports, MRG specialists analysis reports, catastrophic analysis reports, PCP network analysis reports, utilization analysis reports, employer group analysis reports, and hospital analysis reports. The utilization report generator 504d further generates a comparative RVU utilization report comprising the PCP's actual RVU utilization as a ratio to the expected RVU utilization. The utilization analytics database 504e stores the generated reports and information of the utilization analysis of the health care providers 201.

Figure 6:
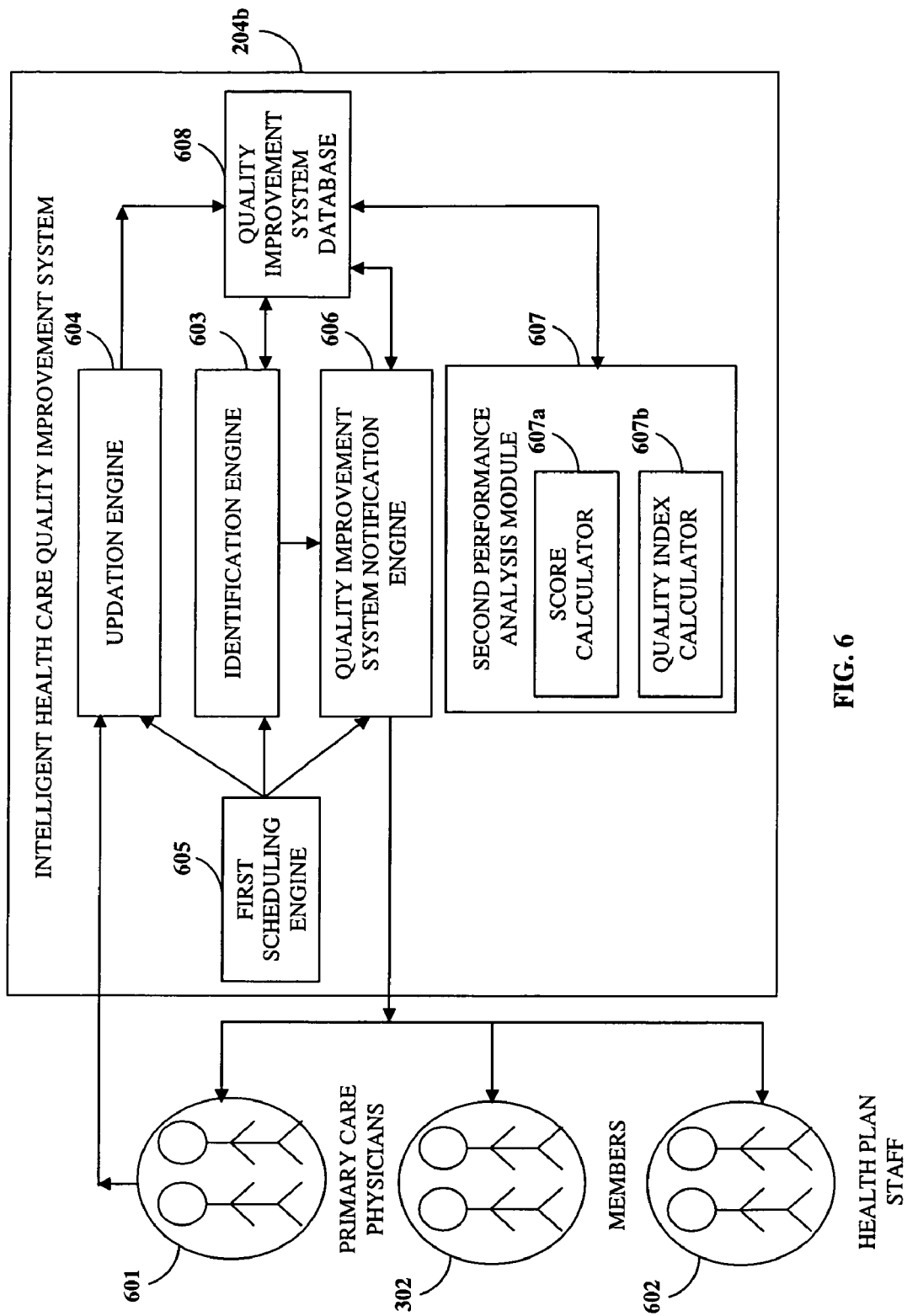
FIG. 6 illustrates an intelligent health care quality improvement system in a health care organization.

FIG. 6 illustrates an intelligent health care quality improvement (IHCQI) system 204b in a health care organization. The IHCQI system 204b evaluates the performance and quality of the PCPs 601 The IHCQI system 204b comprises an identification engine 603, a quality improvement system notification engine 606, an updation engine 604, a second performance analysis module 607, a quality improvement system database 608, and a first scheduling engine 605. The identification engine 603 of the IHCQI system 204b identifies the members 302 of the health plan eligible for undergoing predetermined measures of health care. The predetermined measures required by the members 302 of the health plan are stored in the quality improvement system database 608. The identification engine 603 also identifies the PCPs 601 for the identified members 302. The first scheduling engine 605 schedules the identification, notification of the members 302, and updation of the status of the identified members 302. The updation engine 604 of the IHCQI system 204b provides an online user interface for the PCPs 601 to update the status of the identified members 302 based on the implemented predetermined measures.

The quality improvement system notification engine 606 of the IHCQI system 204b notifies the identified members 302 to undergo the predetermined measures. The second performance analysis module 607 of the IHCQI system 204b comprises a score calculator 607a and a quality index calculator 607b. The score calculator 607a calculates a performance score of the health plan for each of the predetermined measures. The performance score for a predetermined measure of the health plan is the ratio of the number of the members 302 of the health plan already measured for the predetermined measure to the total number of the identified members 302 for that predetermined measure in the health plan. The performance score compares performance of the health plan with predetermined performance benchmarks. The predetermined performance benchmarks are one of national benchmarks and regional benchmarks.

The quality index calculator 607b calculates quality indices for the PCPs 601 for the implemented predetermined measures. The step of calculating the quality indexes for the PCPs 601 comprises calculating an individual quality index for each of the predetermined measures, a relative quality index for each of the predetermined measures, and a total quality index for each of the PCPs 601. The individual quality index is the ratio of the number of members 302 of the PCPs 601 that are already measured for the predetermined measures to the total number of identified members 302 of the PCPs 601. The quality index calculator 607b also calculates the relative quality index for each of the PCPs 601 as the ratio of the performance score of the health plan for each of the predetermined measures to the individual quality index of each of the PCPs 601. The relative quality index for each of the PCPs 601 is given by the following formula:

Relative quality index for a PCP for a predetermined measure=Health Plan's performance score of the predetermined measure/individual quality index of the PCP for that predetermined measure.

The quality index calculator 607b also calculates the total quality index for each of the PCPs 601. The total quality index is calculated as the average of the relative quality indexes of all the predetermined measures for each of the PCPs 601. The formula for the total quality index for each of the PCPs 601 is given below:

Total quality index of a PCP=Sum of the relative quality indexes of all the predetermined measures of the PCP/Number of predetermined measures.

The total quality index for each of the PCPs 601 is compared with a predetermined threshold value to determine performance of the PCPs 601. The total quality index is used for designing pay for performance programs for each of the PCPs 601. The total quality index of each of the PCPs 601 indicates the quality based performance of the PCPs 601 in the health plan. The performance of the PCP is determined by checking whether the total quality index is greater than or lesser than a predefined value. For example, a total quality index lesser than 1 indicates good performance by a PCP, whereas a total quality index greater than 1 indicates that the PCP is required to improve performance.

Effective incentive programs and pay for performance programs may be designed to reward effective PCPs 601 as explained in the detailed description of FIG. 1. The health care administrators may review the performance of the PCPs 601. The PCPs 601 who have not met the required percentage specified by the health plan are notified and reminded to follow-up on their members 302. The PCPs 601 performance may also be compared with national benchmarks for different HEDIS measures. The total quality index of each of the PCPs 601 calculated by the score calculator 607a are stored in the quality improvement system database 608. The analysis of performance ensures increased quality by PCPs 601, reduced level of chart review by the health plan staff 602, improved health of the members 302 and subsequent reduction in overall medical costs.

Figure 7:
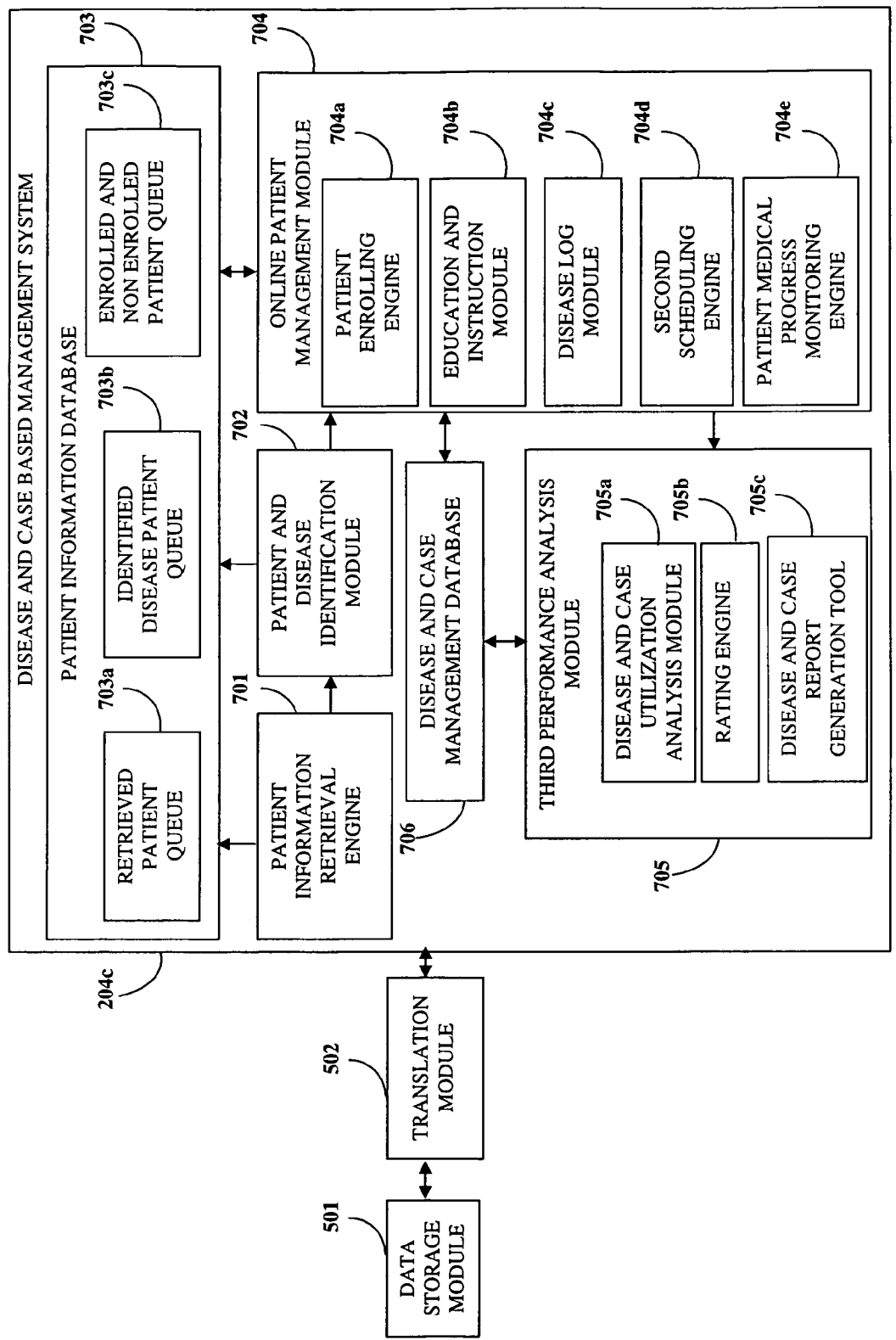
FIG. 7 illustrates a disease and case based management system in a health care organization.

FIG. 7 illustrates a disease and case based management system 204c in a health care organization. The disease and case based management system 204c comprises an online patient management module 704, a patient information retrieval engine 701, a patient and disease identification module 702, a third performance analysis module 705, a patient information database 703, and a disease and case management database 706. The disease and case based management system 204c provides the disease based and case based management of medical care to the patients. Multiple diseases and disease parameters are configured using the disease and case based management system 204c. Further, the disease and case based management system 204c may be accessed any time by patients, health care providers 201, disease managers, case managers, medical directors, and disease management supervisors. The disease and case based management system 204c may be integrated with medical management systems 204 including utilization analytics system 204a, healthcare effectiveness data and information set system 204b, and authorization management system.

The patient information retrieval engine 701 retrieves the raw health care data comprising health plan information of patients of the health care organization, information of the health care providers 201, claims information, and the hospital information. The patient information retrieval engine 701 retrieves the raw health care data from the data storage module 501. The data storage module 501 may also include referrals and authorizations information, information from labs and images, and patient surveys. The patient and disease identification module 702 identifies one of the disease conditions in a patient population and the patients with a disease condition. The disease condition may be monitored and managed based on ICD codes, disease parameter and parameter values, age, and gender of the patient.

The patient information database 703 stores information on one or more of retrieved patient information, identified patient information, enrolled patient information, and non enrolled patient information of the disease and case based management system 204c. The patient information database 703 further comprises a retrieved patient queue 703a, an identified disease patient queue 703b, and an enrolled and non enrolled patient queue 703c. The retrieved patient information is stored in the retrieved patient queue 703a. The identified patient information is stored in an identified disease patient queue 703b. The information on the enrolled patient and non enrolled patient is stored in the enrolled and non enrolled patient queue 703c.

The online patient management module 704 coordinates the disease based and case based management of medical care. The online patient management module 704 further comprises a patient enrolling engine 704a, an education and instruction module 704b, a disease log module 704c, a second scheduling engine 704d, and a patient medical progress monitoring engine 704e. The patient enrolling engine 704a of the online patient management module 704 enrolls the patients for the disease based and case based management of medical care. The patient enrolling engine 704a sends an invitation to the patients for joining the disease based and case based management of medical care based on the availability of an email identity of the patients. If the identified patients possess an email identity, the patient enrolling engine sends the invitation through an electronic mail to the patients. If the patients do not possess an email identity, the patient enrolling engine sends the invitation via automated phone messaging or mail to the patients.

The education and instruction module 704b provides information on self monitoring of a disease condition to the patients. The disease log module 704c records status of the self monitored disease condition by the patients. The self monitored disease condition may be recorded from the residence by the patients. The second scheduling engine 704d schedules a visit to a health care provider for medical treatment of the enrolled patients based on the recorded status. Further, the second scheduling engine 704d synchronizes the online scheduler of the enrolled patients with the online scheduler of the health care provider and a disease manager. The patient medical progress monitoring engine 704e monitors medical progress of the enrolled patients based on the medical treatment. The patient medical progress monitoring engine 704e uses the recorded status in the disease log module 704c to determine the medical status of the enrolled patients. The medical status of the enrolled patients may be one of acute medical status and normal medical status.

The third performance analysis module 705 analyzes the performance of one of the disease manager, the case manager, and the disease based and case based management of medical care of the patients. The third performance analysis module 705 comprises a disease and case utilization analytics engine 705a, a rating engine 705b, and a disease and case report generation tool 705c. The disease and case utilization analysis module 705a performs utilization analysis and clinical outcome analysis of the disease based and case based management of medical care of the patients. The rating engine 705b ranks the health care provider based on performance. The disease and case report generation tool 705c generates reports of the utilization analysis and clinical outcomes analysis of the disease based and case based management.

The disease and case management database 706 stores one or more of list of diseases, international classification of diseases (ICD) diagnosis code, current procedure terminology (CPT) code, national drug classification (NDC) code for each disease, the clinical parameter and parameter values for each disease, education and instruction information, recorded status, patient schedules, and medical progress of the enrolled patients.

Figure 8:
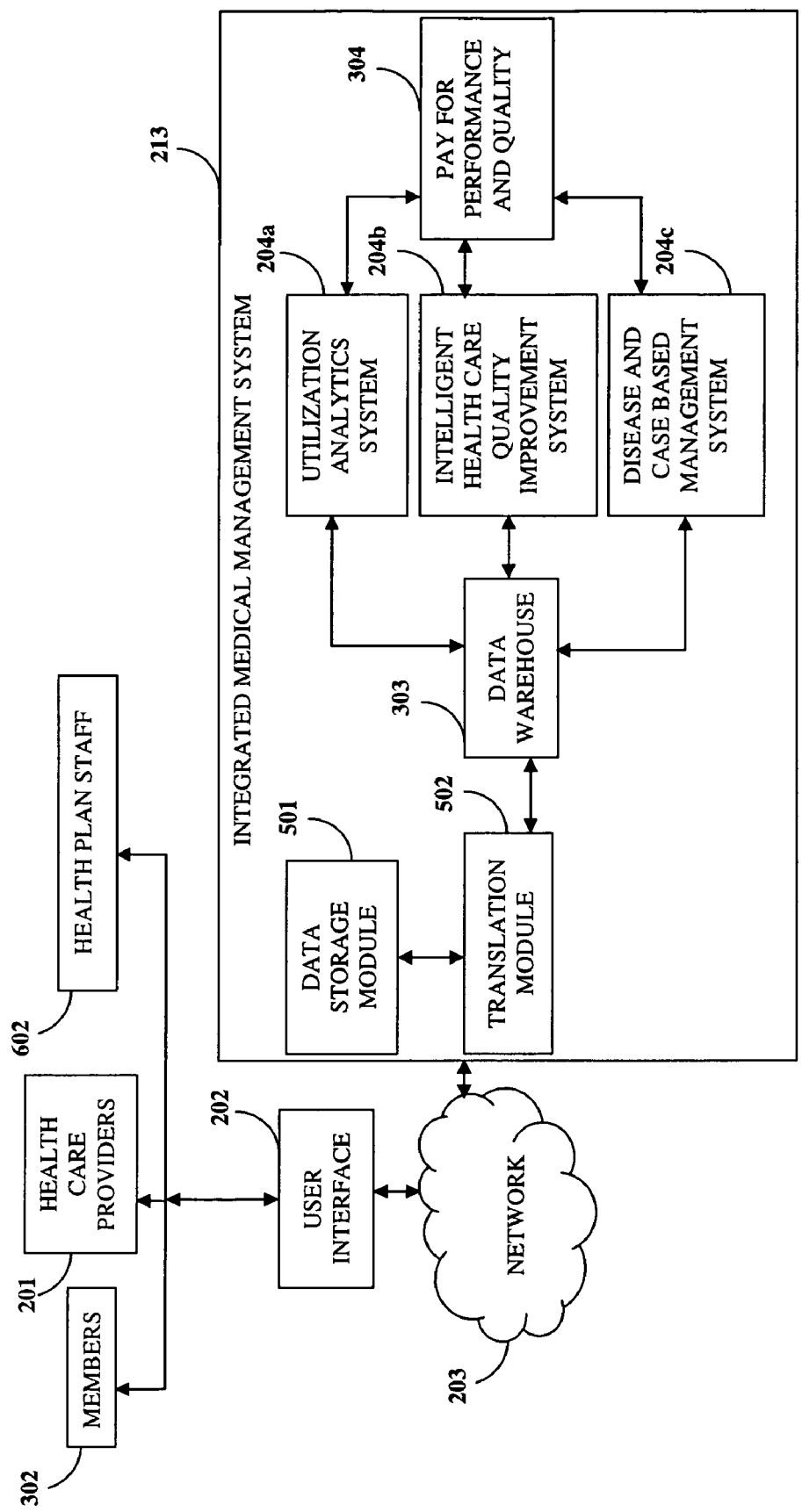
FIG. 8 illustrates an integrated medical management system for pay for performance of health care providers in a health care organization.

FIG. 8 illustrates an integrated medical management system 213 for pay for performance in a health care organization. The integrated medical management system 213 comprises the data storage module 501, the translation module 502, the data warehouse 303, and the medical management systems 204 including the utilization analytics system 204a, the IHCQI system 204b, and the disease and case based management system 204c. The integrated medical management system 213 receives the raw health care data comprising health plan information of members 302 of the health care organization, information of the health care providers 201, claims information, and the hospital information from the data storage module 501. The medical management systems 204 are explained in the detailed description of FIGS. 1-7.

The members 302, the health care providers 201, and the health plan staff 602 access the integrated medical management system 213 through the user interface 202 via the network 203. The translational module 502 translates and organizes the raw health care data in a structured relational format. The data warehouse 303 stores information acquired from databases such as the provider record database 206, the structured relational database 503, the utilization analytics database 504e, the quality improvement system database 608, the patient information database 703, and the disease and case management database 706. The information acquired from the multiple medical management systems 204 is used to analyze performance of the health care providers 201. The health care providers 201 are paid 304 for performance based on utilization and quality of health care provided.

It will be readily apparent that the various methods and algorithms described herein may be implemented in a computer readable medium appropriately programmed for general purpose computers and computing devices. Typically a processor, for e.g., one or more microprocessors will receive instructions from a memory or like device, and execute those instructions, thereby performing one or more processes defined by those instructions. Further, programs that implement such methods and algorithms may be stored and transmitted using a variety of media, for e.g., computer readable media in a number of manners. In one embodiment, hardwired circuitry or custom hardware may be used in place of, or in combination with, software instructions for implementation of the processes of various embodiments. Thus, embodiments are not limited to any specific combination of hardware and software. A 'processor' means any one or more microprocessors, Central Processing Unit (CPU) devices, computing devices, microcontrollers, digital signal processors or like devices. The term 'computer-readable medium' refers to any medium that participates in providing data, for example instructions that may be read by a computer, a processor or a like device. Such a medium may take many forms, including but not limited to, non-volatile media, volatile media, and transmission media. Non-volatile media include, for example, optical or magnetic disks and other persistent memory volatile media include Dynamic Random Access Memory (DRAM), which typically constitutes the main memory. Transmission media include coaxial cables, copper wire and fiber optics, including the wires that comprise a system bus coupled to the processor. Transmission media may include or convey acoustic waves, light waves and electromagnetic emissions, such as those generated during Radio Frequency (RF) and Infrared (IR) data communications. Common forms of computer-readable media include, for example, a floppy disk, a flexible disk, hard disk, magnetic tape, any other magnetic medium, a Compact Disc-Read Only Memory (CD-ROM), Digital Versatile Disc (DVD), any other optical medium, punch cards, paper tape, any other physical medium with patterns of holes, a Random Access Memory (RAM), a Programmable Read Only Memory (PROM), an Erasable Programmable Read Only Memory (EPROM), an Electrically Erasable Programmable Read Only Memory (EEPROM), a flash memory, any other memory chip or cartridge, a carrier wave as described hereinafter, or any other medium from which a computer can read. In general, the computer-readable programs may be implemented in any programming language. Some examples of languages that can be used include C, C++, C#, or JAVA. The software programs may be stored on or in one or more mediums as an object code. A computer program product comprising computer executable instructions embodied in a computer-readable medium comprises computer parsable codes for the implementation of the processes of various embodiments.

Where databases are described such as the databases in the data warehouse 303 including the provider record database 206, the structured relational database 503, the utilization analytics database 504e, the quality improvement system database 608, the patient information database 703, and the disease and case management database 706, it will be understood by one of ordinary skill in the art that (i) alternative database structures to those described may be readily employed, and (ii) other memory structures besides databases may be readily employed. Any illustrations or descriptions of any sample databases presented herein are illustrative arrangements for stored representations of information. Any number of other arrangements may be employed besides those suggested by, e.g., tables illustrated in drawings or elsewhere. Similarly, any illustrated entries of the databases represent exemplary information only; one of ordinary skill in the art will understand that the number and content of the entries can be different from those described herein. Further, despite any depiction of the databases as tables, other formats including relational databases, object-based models and/or distributed databases could be used to store and manipulate the data types described herein. Likewise, object methods or behaviors of a database can be used to implement various processes, such as the described herein. In addition, the databases may, in a known manner, be stored locally or remotely from a device that accesses data in such a database.

The present invention can be configured to work in a network environment including a computer that is in communication, via a communications network, with one or more devices. The computer may communicate with the devices directly or indirectly, via a wired or wireless medium such as the Internet, Local Area Network (LAN), Wide Area Network (WAN) or Ethernet, Token Ring, or via any appropriate communications means or combination of communications means. Each of the devices may comprise computers, such as those based on the Intel® processors, AMD® processors, UltraSPARC® processors, etc. that are adapted to communicate with the computer. Any number and type of machines may be in communication with the computer.

The foregoing examples have been provided merely for the purpose of explanation and are in no way to be construed as limiting of the present method and system disclosed herein. While the invention has been described with reference to various embodiments, it is understood that the words, which have been used herein, are words of description and illustration, rather than words of limitation. Further, although the invention has been described herein with reference to particular means, materials and embodiments, the invention is not intended to be limited to the particulars disclosed herein; rather, the invention extends to all functionally equivalent structures, methods and uses, such as are within the scope of the appended claims. Those skilled in the art, having the benefit of the teachings of this specification, may effect numerous modifications thereto and changes may be made without departing from the scope and spirit of the invention in its aspects.

We claim:

1. A computer implemented method of rewarding health care providers in a health care organization using an integrated medical management system, comprising the steps of:
   providing said integrated medical management system, wherein the integrated medical management system comprises a web application for analyzing performance of said health care providers;
   acquiring information from a plurality of medical management systems using said web application;
   determining performance indices for the health care providers based on said acquired information using the web application, comprising:
      calculating quality indices of said health care providers, wherein said quality indices are based on one or more of predetermined health plan employer data and information set analysis, predetermined disease management analysis, and predetermined quality of healthcare measure;

calculating economic indices of said health care providers, wherein said economic indices are based on one or more of utilization analytics, physician profiling, and authorizations management of a health care provider compared to other health care providers in a health plan; and calculating a relative value unit index, wherein said relative value unit index is based on utilization of relative value units;

analyzing said performance of the health care providers based on said determined performance indices, wherein said step of analyzing the performance comprises identifying the health care providers eligible for a reward; and rewarding said identified health care providers based on said analyzed performance;

whereby said health care organization rewards the health care providers based on the performance of the health care providers.

2. The computer implemented method of claim 1, wherein the health care providers are one or more of primary care physicians, procedurally related group specialists, medically related groups specialists, provider networks, hospitals, and ancillary providers.

3. The computer implemented method of claim 1, wherein said medical management systems include a utilization analytics system, provider profiling system, an intelligent health care quality improvement system, a disease and case based management system, referrals and authorizations management system, and a health risk assessment system.

4. The computer implemented method of claim 1, wherein the acquired information from said medical management systems comprises intelligent health care quality improvement analysis information, disease and case based management information, utilization analytics information, physician profiling information, authorizations management information, lab and imaging information, and health risk assessment information.

5. The computer implemented method of claim 1, wherein the acquired information comprises information of members enrolled with the health care providers, wherein said member information comprises information of health plan benefits, medical claims, pharmacy claims, hospital information, allied health center information, authorizations and referrals information, lab and imaging information, disease conditions, and comorbid conditions of said members.

6. The computer implemented method of claim 1, further comprising a step of updating unobserved performed health care measures by the health care providers.

7. The computer implemented method of claim 1, further comprising a step of notifying the health care providers for performing health care measures.

8. The computer implemented method of claim 7, wherein the integrated medical management system automatically triggers different communication devices for said notification in absence of access of the web application by the health care providers.

9. The computer implemented method of claim 1, wherein the integrated medical management system receives medical information of members via different communication devices in absence of access of the web application by the health care providers.

10. The computer implemented method of claim 9, wherein the integrated medical management system associates said received information with the health care providers of said members and enables updation of the received information.

11. The computer implemented method of claim 1, wherein the step of analyzing the performance comprises a step of monitoring the performance of the health care providers using the web application.

12. The computer implemented method of claim 1, further comprising a step of generating reports on the performance of the health care providers using the web application.

13. The computer implemented method of claim 1, wherein said step of rewarding comprises offering a projected increase in reimbursements to the identified health care providers.

14. The computer implemented method of claim 1, further comprising a step of identifying ineffective health care providers, wherein said identified ineffective health care providers are provided recommendations for improvement on health care management.

15. A computer implemented system for rewarding health care providers in a health care organization based on performance of said health care providers, comprising:

an integrated medical management system, comprising:
  a plurality of medical management systems;
  a web application server comprising:
    an information acquisition module for acquiring information from a plurality of medical management systems;
    a performance index calculation module for determining performance indices for the health care providers, comprising:
      a quality index module for determining quality indices of said health care providers, wherein said quality indices are based on one or more of predetermined health plan employer data and information set analysis, predetermined disease management analysis, and predetermined quality of healthcare measure;
      an economic index module for determining economic indices of said health care providers, wherein said economic indices are based on one or more of utilization analytics, physician profiling, and authorizations management of a health care provider compared to other health care providers in a health plan; and
      a relative value unit index module for calculating a relative value unit index, wherein said relative value unit index is based on utilization of relative value units;
    a performance analysis module for analyzing and monitoring said performance of the health care providers; and
    a pay for performance module for rewarding the health care providers based on said analyzed performance.

16. The computer implemented system of claim 15, wherein said integrated medical management system enables updation of medical information of members received via different communication devices.

17. The computer implemented system of claim 15, wherein said medical management systems comprise an utilization analytics system, an intelligent health care quality improvement system, a disease and case based management system, a provider profiling system, a referrals and authorizations management system, and a health risk assessment system.

18. The computer implemented system of claim 15, further comprising a user interface for enabling health care administrators to assign a predetermined weighted percentage value for said performance indices.

19. The computer implemented system of claim 15, wherein said information acquisition module acquires information comprising intelligent health care quality improvement analysis information, disease and case based management information, utilization analytics information, physician profiling information, authorizations management information, lab and imaging information, and health risk assessment information.

20. The computer implemented system of claim 15, wherein said web application server further comprises a health care measure updation module for updating unobserved performed health care measures.

21. The computer implemented system of claim 15, wherein said web application server further comprises a report generation module for generating reports on the performance of the health care providers.

22. The computer implemented system of claim 15, wherein said web application server further comprises a provider record database for storing said acquired information, updated health care measure information, generated reports, information of said performance indices, analyzed performance information of the health care providers, and reward information of the health care providers.

23. The computer implemented system of claim 15, wherein said web application server further comprises a notification engine for notifying the health care providers to perform health care measures.

24. A computer program product comprising computer executable instructions embodied in a non-transitory computer-readable medium, wherein said computer program product comprises:

a first computer parsable program code for acquiring information from a plurality of medical management systems;

a second computer parsable program code for determining performance indices for health care providers based on said acquired information, comprising:

a quality index module for determining quality indices of said health care providers, wherein said quality indices are based on one or more of predetermined health plan employer data and information set analysis, predetermined disease management analysis, and predetermined quality of healthcare measure;

an economic index module for determining economic indices of said health care providers, wherein said economic indices are based on one or more of utilization analytics, physician profiling, and authorizations management of a health care provider compared to other health care providers in a health plan; and a relative value unit index module for calculating a relative value unit index, wherein said relative value unit index is based on utilization of relative value units;

a third computer parsable program code for analyzing performance of said health care providers based on said determined performance indices;

a fourth computer parsable program code for rewarding the health care providers based on said analyzed performance; and a fifth computer parsable program code for intelligently associating medical information of members received via different communication devices with the health care providers.

* * * * *